United States Patent [19]

Paduano et al.

[11] Patent Number: 4,940,466
[45] Date of Patent: Jul. 10, 1990

[54] METHOD OF ELECTROLYSIS

[76] Inventors: Ann Paduano; Jerome G. Paduano, both of P.O. Box 97, Cold Spring Harbor, N.Y. 11724

[21] Appl. No.: 339,254

[22] Filed: Apr. 17, 1989

[51] Int. Cl.⁵ .................................... A61B 17/41
[52] U.S. Cl. ............................. 606/36; 606/44
[58] Field of Search ............. 128/305.13, 303.17, 128/303.18; 606/36, 44

[56] References Cited

U.S. PATENT DOCUMENTS

| | | | |
|---|---|---|---|
| 2,700,975 | 2/1955 | Hopfinger et al. | 128/303.18 |
| 3,035,580 | 5/1962 | Guiorguiev . | |
| 3,994,300 | 11/1976 | Siddons . | |
| 4,216,775 | 8/1980 | Cottingham . | |
| 4,295,467 | 10/1981 | Mann et al. . | |
| 4,388,924 | 5/1981 | Weissman et al. . | |
| 4,598,709 | 7/1983 | Smith et al. . | |
| 4,784,136 | 11/1988 | Klein . | |
| 4,825,717 | 4/1989 | Wehrli | 128/303.18 |

Primary Examiner—Lee S. Cohen
Attorney, Agent, or Firm—Leonard Belkin

[57] ABSTRACT

A method of removing hair by epilation employing thermolysis in which the probe is inserted into the follicle parallel to the hair shaft, applying multiple bursts of energy to the tip of the probe located adjacent the papilla in an amount for each burst not exceeding 80% of that required to destroy the papilla, followed by applying the same level of energy at intermediate points along the follicle, and repeating the procedure after the hair shaft is removed. Multiple applications of heat are applied to destroy the papilla without damaging the skin. Hair regrowth is minimized by applying the heat at various points along the length of the follicle.

14 Claims, 1 Drawing Sheet

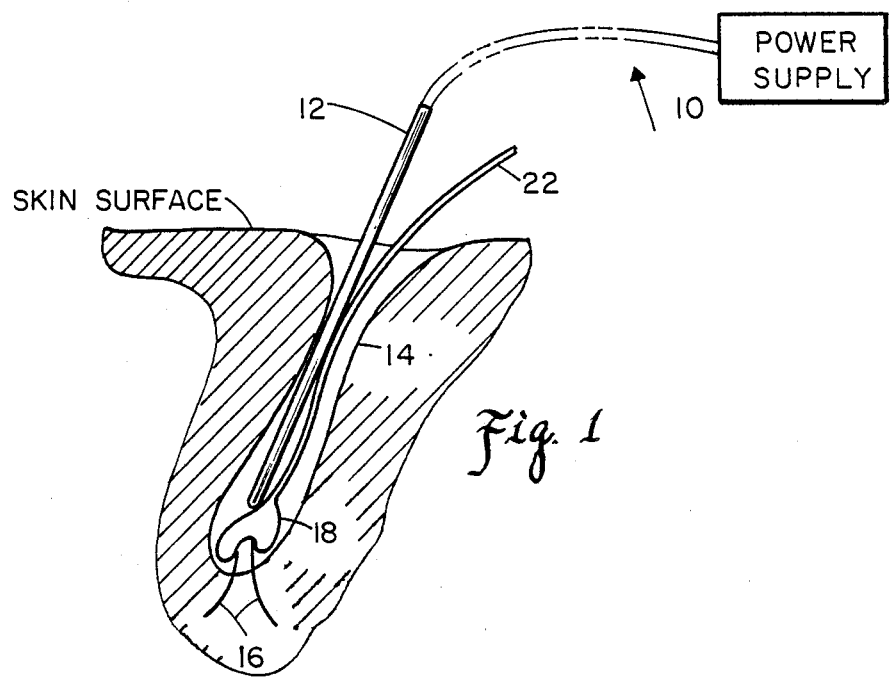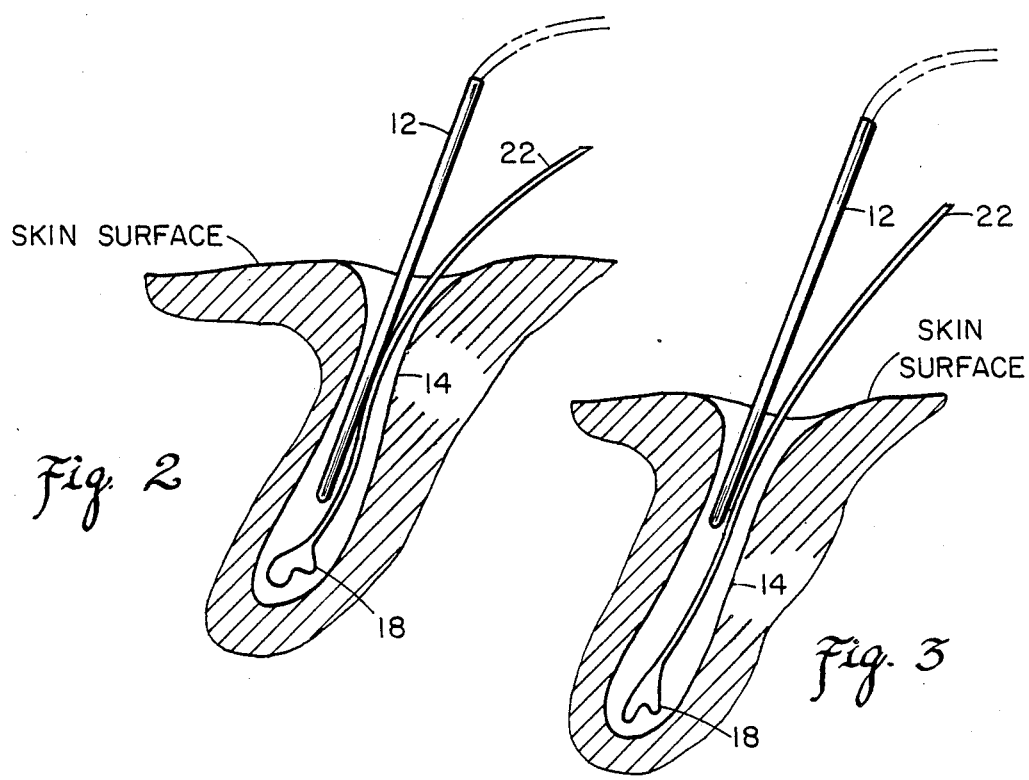

he present invention relates to a method of epilation and more particularly to a method of epilation utilizing an electrolysis technique known as thermolysis.

METHOD OF ELECTROLYSIS

BACKGROUND OF THE INVENTION

The present invention relates to a method of epilation and more particularly to a method of epilation utilizing an electrolysis technique known as thermolysis.

In present methods of electrolysis for the removal of hair from a body, a probe containing a source of electrical energy is inserted into the hair shaft to a depth thought to be the depth of the root, and a burst of electrical energy is applied which is sufficient to destroy the blood vessels delivering blood to the papilla, resulting in its destruction. Tweezers then are employed to remove the hair shaft. The intensity of the energy applied is designed to be fully adequate to destroy the papilla.

There are a number of problems associated with the method of electrolysis as described above. By supplying electrical energy to develop sufficient heat to insure destruction of the papilla, there is as a consequence a certain frequency of skin burns, resulting in some disfiguration because of damage to the skin. In addition, it is quite a common occurrence to have hairs grow out of the same hair shaft, that is regrowth, shortly after the treatment, thereby requiring a repeat of the treatment covering the same area of the skin. This quite often leaves the customer or patient believing that the original treatment was not done properly. In fact, it has been found that what in most cases actually occurs is that one or more young papillas in the follicle is what results in the hair regrowth.

The problems noted above have tended to limit somewhat the acceptance and popularity of electrolysis as a method of hair removal whereas thermolysis is inherently a very safe, effective and economical technique once the problems noted above can be overcome.

The following U.S. Pat. Nos. illustrate current techniques and apparatus for epilation utilizing electrolysis: 3,035,580, 3,994,300, 4,216,775, 4,295,467, 4,388,924, 4,598,709, and 4,784,136. None of the preceding patents teaches or suggest the present invention.

SUMMARY OF THE INVENTION

In this invention the technique of thermolysis for the removal of hair is improved to avoid producing damage to the skin and to insure that once a hair is removed as a result of the procedure new hairs will not normally be growing out of the same follicle.

In accordance with a preferred embodiment of this invention, the probe is inserted into the follicle parallel with the hair shaft down to a depth where the root is located. Then a burst of HF electrical energy is applied having an intensity which is normally substantially less than what is required to destroy the blood vessels in a single burst. The application of energy is repeated with at least three bursts at several, usually three, points along the length of the follicle, until the hair shaft is readily removable using the tweezers. The hair shaft may be gently tugged, and if it is not loose, then additional bursts of energy are applied. Usually three bursts of pulses of energy will result in the hair shaft becoming loose and readily removable. After the hair shaft is removed, the process of applying bursts of energy at a minimum of three points along the follicle is repeated. This will result in destroying any young roots which may exist at intermediate levels and thus limit the number of regrowths. The total amount of energy expended in treating a single follicle is substantially in excess of that which has been applied up to now except the energy employed in each burst is far less than is presently the case.

It is thus a principal object of this invention to provide a method of electrolysis for the removal of hair which is less likely to cause skin damage and less likely to result in hair regrowth.

Other objects and advantages of this invention will hereinafter become obvious from the following detailed description of preferred embodiments of this invention.

BRIEF DESCRIPTION OF THE DRAWING

FIG. 1 is a diagrammatical view showing a probe inserted in a follicle for the removal of a visible hair shaft.

FIG. 2 is a diagrammatical view showing the partial retraction of the probe shown in FIG. 1 for another application of energy.

FIG. 3 is a diagrammatic view showing a further retraction of the probe ready for a subsequent application of energy.

DETAILED DESCRIPTION OF THE PREFERRED EMBODIMENTS

Referring to FIG. 1 there is illustrated thermolysis apparatus or epilator 10 of conventional design including a probe 12 inserted in a hair follicle 14 in preparation for the application of heat utilizing HF energy to cause destruction of blood vessels 16 which will result in the coagulation or destruction of papilla 18 and permit hair shaft 22 to be removed using tweezers (not shown).

Epilator 10 is provided with a foot operated switch (not shown) for the application of power which is in the form of a burst of heating. When the switch is momentarily closed, apparatus 10 will deliver a burst of radio frequency energy in the form of a sequence of electrical power to probe 12. Apparatus 10 is provided with a dial (not shown) for the electrologist to set a timer which determines the intensity of each burst after the switch is pressed, and another dial which sets the duration of pulses being delivered to probe 12. Typically, the duration dial would be graduated 1-10, with 10 representing a full second, on a linear scale.

As is understood in the art, and as described in U.S. Pat. No. 4,598,709, a high frequency voltage is injected into the follicle by producing intense localized heating at the tip of the probe. The heat destroys the blood vessels to the papilla and frees up the hair shaft making it possible to remove the hair shaft without any painful tugging.

Under existing techniques for removing hair using the method just described, the energy setting for the intensity of the bursts is set, according to the specifications of the manufacturer of the apparatus and what is understood among electrologists, at a level which will ordinarily and in almost all cases be adequate to destroy the blood vessels and free up the hair shaft in one burst, although in some cases a second application may be necessary. For an intensity setting of 4.5 watts for a duration of 0.35 second, or 1.575 watt-sec. on average the papilla will be destroyed with one burst of HF energy, although in some cases a second burst may be necessary. The foregoing is based upon information supplied by a manufacturer of typical apparatus used in the manner described.

As earlier noted, under the currently used technique which has just been described, the patient is subject to a significant risk that some skin burning resulting in pain and disfiguration will take place. In addition, hair regrowth is a common and constant problem.

The practice of this invention virtually eliminates the risk of skin damage and reduces the risk of hair regrowth to under 10%. In the long run, the present invention makes it much cheaper to remove hair permanently because of the reduced need for subsequent treatments.

In accordance with a preferred embodiment of this invention, the skin in the area of the follicle selected for treatment is gently stretched to secure the opening into the follicle and probe 12 is inserted into follicle 14 parallel to hair shaft 22 to a depth where the tip of probe 12 is estimated to be adjacent the root, or papilla 18, of hair shaft 22. The depth is determined by pulling out a hair in the region to be treated and measuring the distance along the hair shaft to the papilla.

In order to coagulate the papilla, the electrologist must select the correct amount of high-frequency heating (HF) to use. This is accomplished in the epilator according to this invention by the combination of one dial which sets the duration of current flow to the probe, typically in tenths of a second up to one second and a second dial which selects the intensity. The total energy delivered to the probe in a burst is a combination of the two settings, and it is understood that if the duration is increased the electrologist can compensate by reducing the intensity, and deliver the same amount of total energy, and vice versa.

The settings of the timing dial and the intensity dial are such that the total energy delivered during each burst or application of HF energy is substantially less than what would ordinarily be required to kill or coagulate the papilla. That is, the energy applied in a single burst is at least 50% but not more than 80% of that required to kill or coagulate the papilla, and at least three bursts are given at a time at any particular location.

Based upon the numbers given above, this means that the energy applied in any single burst is between about 0.8 and 1.25 watt-sec., and at least three bursts are given. Three bursts are sufficient to destroy the papilla.

In the practice of this invention, the duration is selected first, usually no more than about 0.3 sec., in order to limit the heat to the tip of the probe where the heat is generated. As the duration is extended, the heat spreads along the length of the probe and is less concentrated in the area of interest. Once the duration dial is set, the level of intensity is determined and the intensity dial is set to that intensity.

Once the electrologist has set the timing and intensity of the bursts, he or she then presses the foot switch in order to initiate the burst. As already indicated, one burst will not result in hair shaft 22 becoming free. The electrologist then presses the foot switch second and third times to produce a total of at least three bursts of energy.

As seen in FIG. 2, the probe is then partially retracted along follicle 14 and the foot switch is pressed again to apply three more bursts, and the procedure is repeated at a third position as shown in FIG. 3. Probe 12 is then withdrawn and tweezers are used to remove hair shaft 22. The total amount of heat delivered in all three bursts at each location should be at least double the amount required to destroy said papilla in a single burst.

After the hair shaft 22 is removed, the preceding procedure at three points along the follicle is repeated, in order to insure that any papillas present along the follicle will be destroyed.

If the procedure as described above is followed, there is virtually no risk of damage to the skin, and hair regrowth will be limited to less than 10%, based up experience in following the described procedure. It will also be noted that the procedure described in carrying out the principles of this invention delivers far more HF energy to the follicle than methods practiced up to now, while at the same time reducing substantially the risk of any harmful effects such as disfiguration due to burning.

While only a single preferred of the invention has been described it is understood that many variations are possible without departing from the principles of this invention as defined in the claims which follow.

What is claimed is:

1. A method of epilation by thermolysis comprising the steps of:
   a. inserting a probe having a tip into a follicle containing a hair shaft, with said tip of said probe terminating adjacent the papilla of said hair shaft, said probe being connected to apparatus for delivering upon actuation to said probe a burst of high frequency energy to produce heat in the tip of said probe, said apparatus comprising means to establish the duration of said burst and means to select the intensity of said burst, the combination of the duration established and the intensity selected representing the total heat energy delivered in each burst to the tip of said probe to the follicle;
   b. selecting a combination of duration and intensity for each burst so that the total heat energy of each said burst is a least about 50% but no more than about 80% of that ordinarily required to coagulate said papilla;
   c. applying multiple such bursts of energy to said probe;
   d. partially withdrawing said probe so that said tip is located at some intermediate point along the length of said follicle;
   e. applying multiple said bursts of energy to said probe;
   f. partially withdrawing further said probe so that said tip is located at some further intermediate point along the length of said follicle;
   g. applying multiple said bursts of energy to said probe;
   h. withdrawing said probe out of said follicle;
   i. removing said hair shaft; and
   j. repeating the preceding steps of applying multiple said bursts of energy at three spaced points along said follicle.

2. The method of epilation as recited in claim 1 in which at least three said bursts of energy are applied to said probe with its tip adjacent said papilla.

3. The method of epilation as recited in claim 1 in which at least three said bursts are applied at all positions of said probe.

4. A method of epillation of hair by thermolysis comprising the steps of:
   a. inserting a probe having a tip into a follicle containing a hair shaft, with said tip of said probe terminating adjacent the papilla of said hair, said probe being connected to means for producing in the tip of said probe a burst of heat by the application of HF energy comprising first means to establish the duration of said burst and second means to select the intensity of energy in said burst, the total energy being delivered in each said burst being the combination of said duration and intensity;

b. delivering multiple such bursts of energy to said tip no more than about 80% of that required in each burst to coagulate said papilla;

c. repeating the delivery of said bursts at two other spaced locations along the length of said follicle;

d. withdrawing said probe out of said follicle;

e. removing said hair shaft; and f. reinserting said probe into said follicle repeating the delivery of said bursts along the length of said follicle, the total energy being delivered by all of said bursts to said follicle being in excess of twice the energy required to destroy said papilla.

5. The method of epilation as recited in claim 4 in which more than two said bursts of said pulses are applied to said probe with its tip at the bottom of said follicle in the presence of said hair shaft.

6. The method of epilation as recited in claim 4 in which more than two said bursts are applied to all positions of said probe in the presence of said hair shaft.

7. The method of epilation as recited in claim 4 in at least three said bursts are applied in all positions of said probe.

8. The method of epilation as recited in claim 4 in which each burst of energy does not exceed 1.25 watt-sec.

9. The method of epilation as recited in claim 4 in which each burst of energy is at least about 0.8 watt-sec.

10. The method of epilation as recited in claim 4 in which each burst of energy is in the range of between about 0.8 and 1.25watt-sec.

11. The method of epilation as recited in claim 4 in which the duration is set at no more than about 0.3 sec.

12. A method of epilation by thermolysis comprising the steps of:

a. inserting a probe having a tip into a follicle containing a hair shaft, with said tip of said probe terminating adjacent the papilla of said hair shaft, said probe being connected to apparatus for delivering upon actuation to said probe a burst of high frequency energy to produce heat in the tip of said probe, said apparatus comprising means to establish the duration of said burst and means to select the intensity of said burst, the combination of the duration established and the intensity selected representing the total heat energy delivered in each burst to the tip of said probe to the follicle;

b. selecting a combination of duration and intensity for each burst so that the total heat energy of each said burst is insufficient to coagulate said papilla;

c. applying multiple such bursts of energy to said probe;

d. partially withdrawing said probe so that said tip is located at some intermediate point along the length of said follicle;

e. applying multiple said bursts of energy to said probe;

f. partially withdrawing further said probe so that said tip is located at some further intermediate point along the length of said follicle;

g. applying multiple said bursts of energy to said probe, the total energy being delivered by all of said bursts to said follicle being in excess of twice the energy required to destroy said papilla;

h. withdrawing said probe out of said follicle; and i. removing said hair shaft.

13. The method of claim 12 in which the heat energy in each said burst is no more than 80% of that required to coagulate said papilla.

14. The method of claim 13 in which the heat energy in each said burst is at least 50% of that required to coagulate said papilla.

* * * * *